US009144832B2

(12) United States Patent
Yamazaki et al.

(10) Patent No.: US 9,144,832 B2
(45) Date of Patent: Sep. 29, 2015

(54) NEEDLE WASHING MECHANISM

(71) Applicant: Shimadzu Corporation, Kyoto-Shi (JP)

(72) Inventors: Tomoyuki Yamazaki, Kyoto (JP); Przemyslaw Stasica, Hertfordshire (GB); Bob Boughtflower, Hertfordshire (GB)

(73) Assignee: Shimadzu Corporation, Kyoto-Shi (JP)

( * ) Notice: Subject to any disclaimer, the term of this patent is extended or adjusted under 35 U.S.C. 154(b) by 86 days.

(21) Appl. No.: 13/893,090

(22) Filed: May 13, 2013

(65) Prior Publication Data

US 2013/0306117 A1 Nov. 21, 2013

(30) Foreign Application Priority Data

May 15, 2012 (JP) .................. 2012-111174

(51) Int. Cl.
*B08B 9/00* (2006.01)
*G01N 35/10* (2006.01)

(52) U.S. Cl.
CPC .............. *B08B 9/00* (2013.01); *G01N 35/1004* (2013.01)

(58) Field of Classification Search
CPC .............. G01N 30/02; G01N 35/1004; G01N 35/1079; G01N 35/1097; G01N 35/00; G01N 35/10; G01N 35/1083; G01N 35/1095; G01N 30/18; G01N 30/20; G01N 30/24; G01N 30/06; G01N 30/08; G01N 30/26; G01N 30/32; G01N 30/34; G01N 30/462; G01N 30/80; G01N 30/82; G01N 30/72; G01N 30/00; G01N 30/10; G01N 30/1083; G01N 30/1095; B01D 15/08; B01D 15/424; B08B 3/04; B08B 9/00; B08B 9/02; B08B 9/032; B08B 9/0323; B08B 9/0328
USPC ......... 134/171, 170, 169 R, 166 C, 21, 22.12, 134/198, 22.11; 210/656; 73/61.52, 61.55, 73/864.22; 239/106; 422/63, 510, 64, 514, 422/65

See application file for complete search history.

(56) References Cited

U.S. PATENT DOCUMENTS 6,344,034 B1 * 2/2002 Sudo et al. .................... 604/263
7,337,653 B2 * 3/2008 Togashi et al. ............... 73/61.56
(Continued)

FOREIGN PATENT DOCUMENTS

CN 102236024 A 11/2011
JP S53-057893 U1 10/1976
(Continued)

OTHER PUBLICATIONS

Examination Report Received for Chinese Patent Application No. 201310177924.4, mailed on Mar. 26, 2015, 8 pages. (2 pages of English Translation and 6 pages of Official Copy).
(Continued)

*Primary Examiner* — Michael Barr
*Assistant Examiner* — Tinsae Ayalew
(74) *Attorney, Agent, or Firm* — Morgan, Lewis & Bockius LLP

(57) ABSTRACT

A needle washing mechanism allowing the selection of an appropriate needle cleaning liquid without having to take volatility into consideration is presented. The needle washing mechanism has: needles standing on a base side by side and each of which has a path inside thereof through which a liquid passes; washing ports having washing holes including openings; and a needle cleaning liquid supply means for supplying a needle cleaning liquid to each of the washing holes, and includes cap sections, which are provided on the outer circumferential surface of the needles, for closing the openings of the washing holes when the needles are inserted into the washing holes. The washing ports are biased toward the openings by means of biasing means. In addition, disposal passages for discharging the needle cleaning liquid from the washing holes are provided in the washing ports.

6 Claims, 3 Drawing Sheets

(56) References Cited

U.S. PATENT DOCUMENTS

| | | | |
|---|---|---|---|
| 7,500,386 B2 * | 3/2009 | Togashi et al. | 73/61.55 |
| 7,526,947 B2 * | 5/2009 | Tatsumi et al. | 73/61.55 |
| 2006/0102502 A1 * | 5/2006 | Biscotti | 206/363 |

FOREIGN PATENT DOCUMENTS

| | | |
|---|---|---|
| JP | 2002-340876 A | 11/2002 |
| JP | 2003-149217 | 5/2003 |
| WO | WO 2009/044427 A1 | 4/2009 |
| WO | 2011/085285 A1 | 7/2011 |

OTHER PUBLICATIONS

First Office Action issued in the corresponding Japanese Patent Application No. 2012-111174 dated Jul. 7, 2015 (English summary attached).

* cited by examiner

NEEDLE WASHING MECHANISM

TECHNICAL FIELD

The present invention relates to a needle washing mechanism which is used in a preparative separation-purification system and other systems.

BACKGROUND ART

In the pharmaceutical industry and other fields, for example, preparative separation-purification systems utilizing a liquid chromatograph are used to collect samples of a variety of chemically synthesized compounds in order to store those samples in a library or analyze them in more detail. Conventional examples of the preparative separation-purification system are disclosed in Patent Documents 1 and 2.

In those conventional apparatuses, target components are collected from a sample solution as follows. First, target components (compounds) in a sample solution are temporally separated by a liquid chromatograph. The separated target components are then respectively introduced into different trap columns and temporarily captured therein. Subsequently, a solvent is supplied into each trap column to elute the component from the trap column and collect it in a container. Thus, a plurality of eluates each containing one target component at a high concentration is respectively collected in a plurality of containers. These separately collected solutions are then subjected to a vaporizing and drying process to remove the solvent and collect the target components in solid forms.

In such a preparative separation-purification system, a needle is used with a passage inside thereof which allows a liquid to pass through. For example, a cleaning liquid (column cleaning liquid) for washing off impurities other than the target components captured in the trap column flows through the passage of the needle, and a solvent (eluting solvent) for eluting the target components flows through the passage into the washed trap column. A pipe through which the column cleaning liquid is supplied or a pipe through which the eluting solvent is supplied is connected to the base of the needle. The tip of the needle is inserted into a needle port which is provided at the inlet end of the trap column. This connects the pipe and the trap column. Since different liquids are supplied to the different needles, a column cleaning liquid supply needle and an eluting solvent supply needle are separately provided. In order to use a common driving mechanism for the two needles to simplify the system configuration, the needles stand in a base side by side. That is, the single base is driven to move the two needles to a vicinity of a desired trap column, and then the base is moved more precisely to connect a desired needle to the target trap column.

As described above, a column cleaning liquid supply needle and an eluting solvent supply needle are provided. When the needle is disconnected from the trap column, components captured in the trap column and other substances remain in a circumferential portion of the tip of the needle. If the needle with such residual components adhered to its tip is connected to the next trap column, the residual components enter the trap column, which causes a contamination. In view of this, conventionally, every time the supply of a column cleaning liquid or an eluting solvent to a column is finished, the tips of the needles are washed using a needle washing mechanism as shown in FIG. 5.

In the conventional needle washing mechanism shown in FIG. 5, two washing holes 91a and 91b with an upwardly-open opening are provided with a distance therebetween corresponding to the distance between two needles 19a and 19b, so that the two needles 19a and 19b can be simultaneously washed. After a base 40 is driven to insert the needles 19a and 19b into the washing holes 91a and 91b, respectively, a needle cleaning liquid is supplied to the passages provided inside the needles 19a and 19b by the needle cleaning liquid supply means 100. The needle cleaning liquid flows out from the tips of the needles 19a and 19b and fills the washing holes 91a and 91b. Then, the needle cleaning liquid overflows from openings 92a and 92b at the top of the washing holes 91a and 91b, and is collected in a tray which is not shown. This process removes the residual components attached to the circumferential portion of the tips of the needles 19a and 19b.

BACKGROUND ART DOCUMENT

Patent Documents

[Patent Document 1] WO-A 2009/044427
[Patent Document 2] JP-A 2003-149217

DISCLOSURE OF THE INVENTION

Problem to be Solved by the Invention

In the above-described conventional needle washing mechanism, the upper portions of the washing holes 91a and 91b are open as shown in FIG. 5. Hence, in the case where an organic solvent having a high volatility is used as the needle cleaning liquid, the needle cleaning liquid which has overflowed from the washing holes 91a and 91b volatizes and diffuses into the air, which is a concern in terms of environmental contamination. Therefore, usable needle cleaning liquids are limited to those with a low volatility, such as water. This causes a problem in that the needles cannot be sufficiently washed depending on the kind of residual components attached to the needles.

Such a problem occurs not only in a needle washing mechanism provided in the aforementioned preparative separation-purification system, but also in a needle washing mechanism for washing a needle or needles used for supplying a sample solution to a passage or for changing the passage configuration of a liquid chromatograph apparatus, an auto sampler, and other devices.

The present invention has been achieved to solve the aforementioned problem, and the objective thereof is to provide a needle washing mechanism allowing the selection of an appropriate needle cleaning liquid without having to take volatility into consideration.

Means for Solving the Problem

To solve the aforementioned problem, the present invention provides a needle washing mechanism having: a plurality of needles which stand on a base side by side and each of which has a path inside thereof through which a liquid passes; a plurality of washing ports each of which has a washing hole having an opening into which any one of the needles is inserted; and a needle cleaning liquid supply means for supplying a needle cleaning liquid to each of the washing holes, the needle washing mechanism including:

a) a cap section, which is provided on an outer circumferential surface of each of the plurality of needles, for closing the opening of each of the washing hole when the needle is inserted into the washing hole;
   b) a biasing means for biasing each of the plurality of washing ports toward the opening; and c) a disposal passage, which is provided in the washing port, for discharging the needle cleaning liquid from each of the plurality of the washing holes.

The needle cleaning liquid supply means of the present invention may supply the needle cleaning liquid to each of the washing holes through the path provided in the needles. Alternatively, the needle cleaning liquid supply means may supply the needle cleaning liquid to each of the washing holes through a needle cleaning liquid supply passage which is open on an inner circumferential surface or on an inner bottom surface of the washing holes.

With the needle washing mechanism according to the present invention, when each of the needles is inserted into the washing hole, the cap section provided on the outer circumferential surface of the needle closes the opening of each washing hole. In this state, a needle cleaning liquid is supplied from the needle cleaning liquid supply means to each of the washing holes to wash the circumferential portion of the tip of the needle. Usually, the supplied amount of the needle cleaning liquid is more than necessary to fill the washing hole for a better washing effect. In contrast, with the needle washing mechanism according to the present invention, since each of the cap sections closes each opening, the needle cleaning liquid supplied in excess of the capacity of the washing hole will be discharged from the washing hole through the disposal passage without overflowing from the opening of each of the washing holes. The discharged needle cleaning liquid may be collected with a disposal container or the like so as to prevent the needle cleaning liquid from volatizing and diffusing into the air.

If the attachment positions of the cap sections are different even slightly in the longitudinal direction of the needles, the cap sections may not be able to exhibit the same sealing performance. In such a case, a liquid leakage might occur through the gap between the opening of the washing hole and either of the cap sections. To avoid this problem, in the present invention, the biasing means for biasing each of the washing ports toward the opening is provided in each of the washing ports, thereby canceling the difference between the attachment positions of the cap sections.

The present invention can be applied to various systems, such as a preparative separation-purification system, a liquid chromatograph apparatus, an auto sampler, or other apparatuses in which a needle is used for providing a sample solution to a passage or for changing passages.

Effects of the Invention

As described above, with the needle washing mechanism according to the present invention, the needle cleaning liquid supplied into the washing hole will not volatilize and diffuse into the air, but will be discharged from the washing hole through the disposal passage. This allows a selection of an appropriate needle cleaning liquid without having to take volatility into consideration.

BEST MODES FOR CARRYING OUT THE INVENTION

Figure 1:
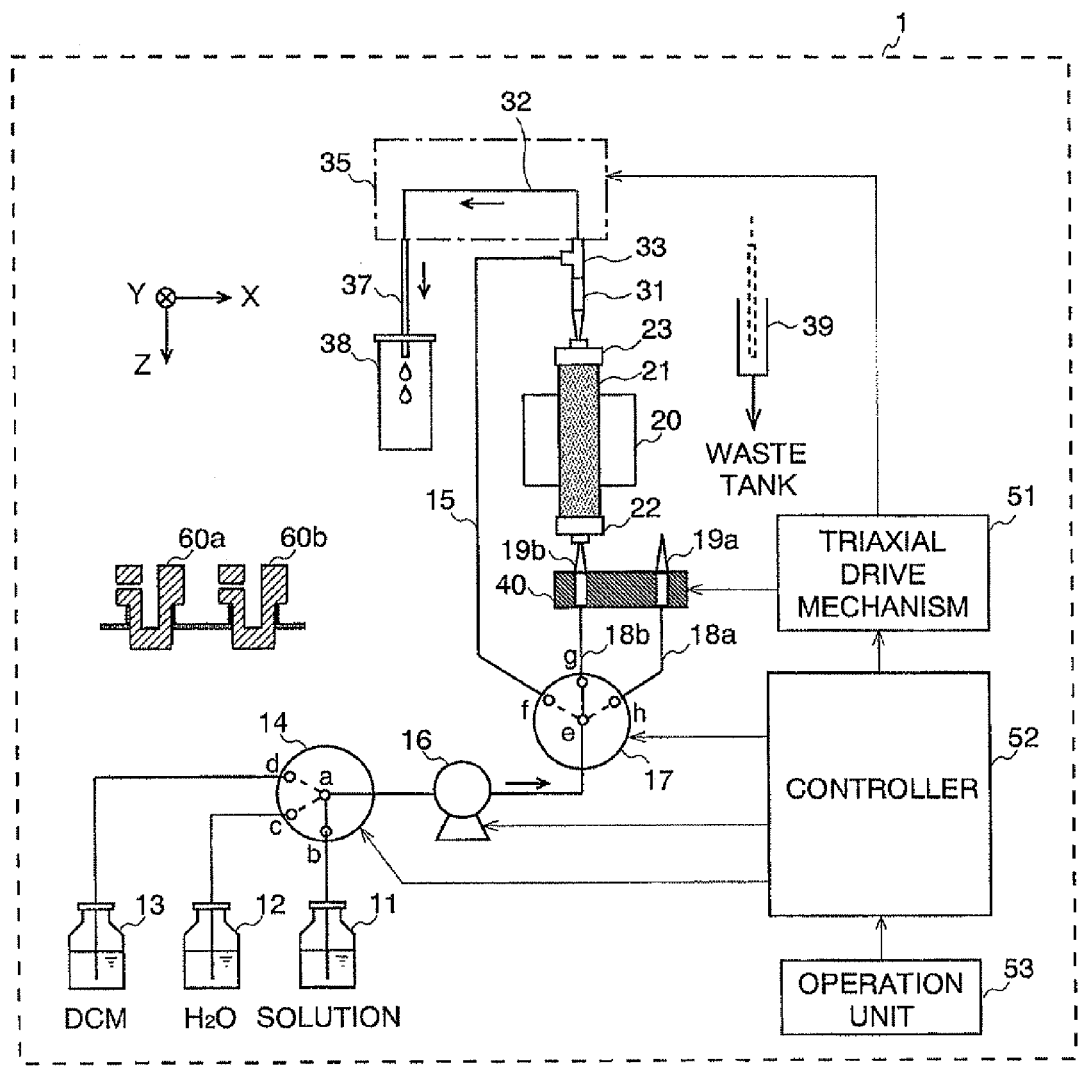
FIG. 1 is a block configuration diagram illustrating the main components of a preparative separation-purification system having a needle port according to an embodiment of the present invention.
Figure 2:
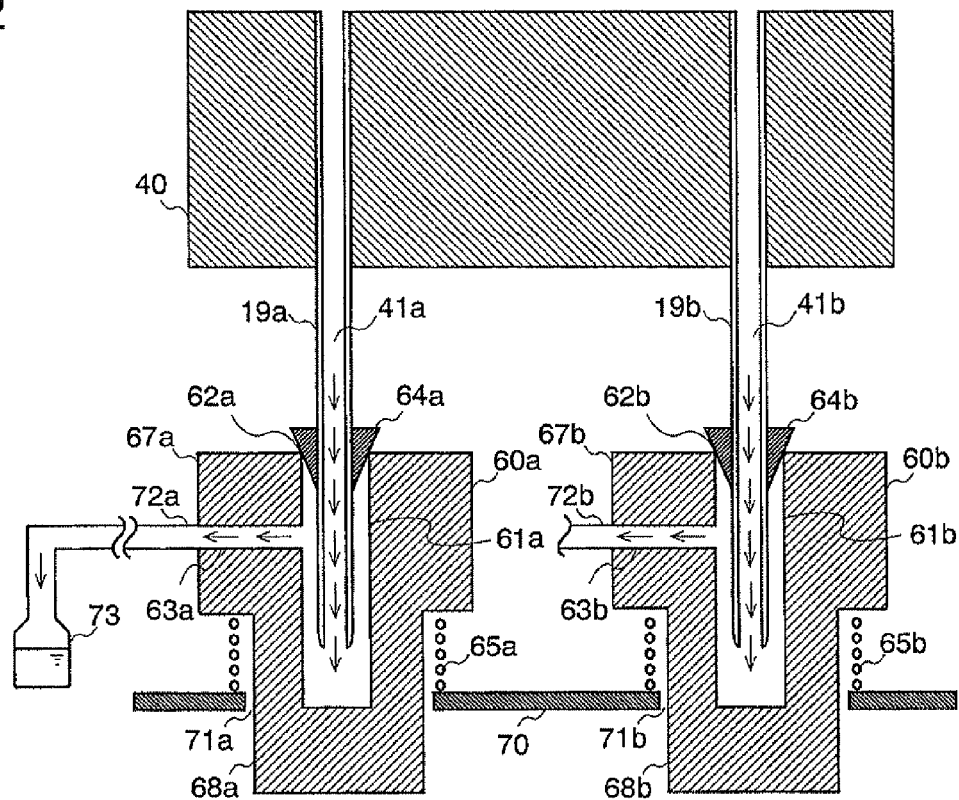
FIG. 2 is a vertical sectional view of a needle washing mechanism according to the present embodiment.

An embodiment of the needle washing mechanism according to the present invention is described in detail with reference to FIGS. 1 and 2. FIG. 1 is a block configuration diagram illustrating the main components of a preparative separation-purification system having a needle port according to an embodiment of the present invention. FIG. 2 is a vertical sectional view of the needle washing mechanism according to the present embodiment. The arrows in FIG. 1 indicate the flowing direction of liquids.

The needle washing mechanism of the present embodiment is provided in a preparative separation-purification system 1. The preparative separation-purification system 1 is for collecting a target component in a solution containing the target component which has been separately collected by a separation-collection liquid chromatograph (not shown), and purifying and obtaining it in a solid form. Alternatively, the separation-collection liquid chromatograph may be directly connected to the previous stage so as to directly introduce the solution containing the target component which has been separated by the separation-collection liquid chromatograph.

A solution container 11 holds a solution containing the target component which has been separately collected in advance as previously described. The solvent of the solution is mainly the mobile phase used in the separation-collection liquid chromatograph. A column wash solution container 12 holds pure water, and an eluting solvent container 13 holds dichloromethane (which is labeled as "DCM" in the figure). In the present embodiment, the dichloromethane held in the eluting solvent container 13 is also used as a needle cleaning liquid (which will be described later). A selector valve 14 is provided to change the passage configuration so that one of the liquids held in these containers 11, 12, and 13 is selectively supplied to the selected passage on which a supply pump 16 for drawing and sending a liquid at a predetermined flow rate is provided.

A selector valve 17 is provided to change the passage configuration so that the liquid sent from the supply pump 16 selectively flows to one of the passages 18a and 18b, and a dilution passage 15. The pipe extending from the supply pump 16 is connected to port e. The other ends of dilution passage 15 and the passages 18b and 18a are connected to port f, port g, and port h, respectively. The other ends of the passages 18a and 18b are connected, respectively, to the bases of the needles 19a and 19b having paths 41a and 41b inside thereof through which a liquid passes. The needle 19a is for supplying the pure water held in the column wash solution container 12 to a trap column 21 (which will be described later). The needle 19b is for supplying the dichloromethane held in the eluting solvent container 13 to the trap column 21. The other end of the dilution passage 15 is connected to a discharge passage 32 (which will be described later) by way of a T-joint 33 provided in the vicinity of the needle 31. This allows a liquid (i.e. dilution liquid) which passes through the dilution passage 15 to directly flow into the discharge passage 32.

The needles 19a and 19b stand on a base 40 side by side. The base 40 can be moved vertically (i.e. in the Z-axis direction in the figure) and horizontally (i.e. in the X-axis and Y-axis directions in the figure) by means of a triaxial drive mechanism 51.

The inside of the trap column 21 is filled with grains of filler which can adsorb the target component. The trap column 21 is held in a substantially vertical position by a column rack 20 so that the inlet end 22 is directed downwards and the outlet end 23 is directed upwards. Although FIG. 1 shows only one trap column 21, actually, a plurality of trap columns 21 is held side by side in the Y-axis direction in the figure (i.e. in the direction perpendicular to the document). A needle port is provided at the inlet end 22 of the trap column 21. Inserting the tip of one of the needles 19*a* and 19*b* connects the trap column 21 with one of the passages 18*a* and 18*b*.

Another needle port is provided at the outlet end 23 of the trap column 21. Inserting the tip of the needle 31 attached to an end of the discharge passage 32 into the needle port connects the trap column 21 with the discharge passage 32. The other end of the discharge passage 32 is connected to the base of a discharge nozzle 37 which has a cylindrical shape. The liquid discharged from the tip of the discharge nozzle 37 is dripped into any one of the collection containers 38 which are aligned in the Y-axis direction in the figure (i.e. in the direction perpendicular to the drawing sheet).

The discharge passage 32, the needle 31, and the discharge nozzle 37 are attached to a fraction collector head 35, which can be moved vertically (i.e. in the Z-axis direction in the figure) and horizontally (i.e. in the X-axis and Y-axis directions in the figure) by means of the triaxial drive mechanism 51. By horizontally moving the fraction collector head 35, the needle 31 can be moved above a desired trap column 21 among the plurality of trap columns 21 held in the column rack 20, and the discharge nozzle 37 can be moved above a desired collection container 38 among the plurality of collection containers 38. A disposal port 39 including a liquid reservoir and a disposal passage which is connected to a waste tank (not shown) is provided in the moving range of the fraction collector head 35 by means of the triaxial drive mechanism 51.

A controller 52 including a central processing unit (CPU) and other components automatically performs a preparative separation-purification task by switching the valves 14 and 17, controlling the driving operation of the triaxial drive mechanism 51, controlling the operation of the supply pump 16 (flow rate or flow speed), and performing other operations according to a previously prepared program. The conditions for the preparative separation-purification task and other information are input and set by means of the operation unit 53.

As described above, the preparative separation-purification system 1 according to the present embodiment includes the needle washing mechanism for washing the needles 19*a* and 19*b*. Hereinafter, the needle washing mechanism is described in detail.

As shown in FIG. 2, the needle washing mechanism includes two washing ports 60*a* and 60*b*, and one bottom plate 70. In the bottom plate 70, two through-holes 71*a* and 71*b* for the attachment of the washing ports 60*a* and 60*b* are formed with a distance therebetween corresponding to the distance between the needles 19*a* and 19*b*. The washing ports 60*a* and 60*b* respectively include lower portions 68*a* and 68*b* and upper portions 67*a* and 67*b*. The lower portions 68*a* and 68*b* have a cylindrical shape with an outside diameter smaller than that of the through-holes 71*a* and 71*b*. The upper portions 67*a* and 67*b* have a cylindrical shape with an outside diameter larger than that of the through-holes 71*a* and 71*b*. The washing ports 60*a* and 60*b* are attached from above to the through-holes 71*a* and 71*b* so as to be loosely fit in such a manner as to be vertically movable with respect to the bottom plate 70. Elastic members 65*a* and 65*b*, which are coil-springs, are inserted between the lower surface of the upper portions 67*a* and 67*b* and the upper surface of the bottom plate 70, thereby biasing upwards the washing ports 60*a* and 60*b*. In place of the coil-springs, a cushioning or other members may be used as the elastic members 65*a* and 65*b*.

Washing holes 61*a* and 61*b* each of which has a bottom and an open top are provided in the washing ports 60*a* and 60*b*. In the process of washing the needles 19*a* and 19*b*, these needles 19*a* and 19*b* are simultaneously inserted from the openings 62*a* and 62*b* provided at the top of the washing holes 61*a* and 61*b* into the washing holes 61*a* and 61*b*.

In the process of washing the needles 19*a* and 19*b*, a needle cleaning liquid is introduced from the base side of the needles 19*a* and 19*b* into the paths 41*a* and 41*b* of the needles. The needle cleaning liquid which has passed through the paths 41*a* and 41*b* is discharged from the tips of the needles 19*a* and 19*b* in order to flow into the washing holes 61*a* and 61*b*. Then, the needle cleaning liquid is discharged from the disposal passages 63*a* and 63*b* respectively provided in the washing port 60*a* and 60*b*. The disposal passages 63*a* and 63*b* are through-holes which connect the inner circumferential surface of the washing holes 61*a* and 61*b* and the outer circumferential surface of the washing ports 60*a* and 60*b*. The disposal passages 63*a* and 63*b* are connected to the disposal container 73 via disposal tubes 72*a* and 72*b*, respectively.

Cap sections 64*a* and 64*b* projecting radially from the outer circumferential surface of the needles 19*a* and 19*b* are provided in an intermediate section in the longitudinal direction of the needles 19*a* and 19*b*. The cap section 64*a* and 64*b* have a tapered shape which becomes thinner toward the tip of the needles 19*a* and 19*b*. Their smallest outside diameter is smaller than the diameter of the openings 62*a* and 62*b* of the washing holes 61*a* and 61*b*, while their largest diameter is larger than the diameter of the openings 62*a* and 62*b*. Therefore, when the needles 19*a* and 19*b* are inserted into the washing holes 61*a* and 61*b* to a predetermined depth, the openings 62*a* and 62*b* of the washing holes 61*a* and 61*b* are closed by the cap sections 64*a* and 64*b*.

Next, the operation of the preparative separation-purification system 1 having the needle washing mechanism of the present embodiment is described. First, in order to capture the target component into the grains of filler inside the trap column 21, the controller 52 connects the solution container 11 (port b) and the supply pump 16 (port a) by means of the selector valve 14. Further, the controller 52 connects the supply pump 16 (port e) and the passage 18*a* (port h) by means of the selector valve 17. The controller 52 drives the base 40 by means of the triaxial drive mechanism 51 so as to insert the tip of the needle 19*a* into the needle port of the inlet end 22 of the trap column 21, thereby connecting the passage 18*a* to the trap column 21. In addition, the needle 31 is inserted into the needle port of the outlet end 23 of the trap column 21, and the discharge nozzle 37 is inserted into the disposal port 39. From this state, the supply pump 16 is energized to supply a liquid at a predetermined flow rate. Then, the supply pump 16 draws the solution held in the solution container 11 and delivers it through the inlet end 22 to the trap column 21. When the solution flows through the trap column 21, the target component contained in the solution is captured by the grains of filler. The mobile phase from which the target component has been removed passes through the outlet end 23, the discharge passage 32, and the discharge nozzle 37, and is disposed into the disposal port 39.

After the solution is supplied into the trap column 21 for a predetermined period of time or until the solution prepared in the solution container 11 is exhausted, the controller 52 switches the selector valve 14 to connect the column wash solution container 12 (port c) and the supply pump 16 (port a). Then, the supply pump 16 draws pure water from the column wash solution container 12 and delivers it through the inlet end 22 into the trap column 21. By this process, any unwanted water-soluble substance (e.g. salt) adhered to the grains of filler in the previous process of capturing the target component is removed from the inside of the trap column 21. The target component captured on the grains of filler can barely elute into the water due to its strong adsorption effect. Therefore, the target component remains in the captured state within the trap column 21.

After the pure water has been supplied into the trap column 21 for the predetermined time or to a predetermined amount, the controller 52 connects the eluting solvent container 13 (port d) and the supply pump 16 (port a) by means of the selector valve 14, and connects the supply pump 16 (port e) and the passage 18b (port g) by means of the selector valve 17. The controller 52 also energizes the base 40 to disconnect the needle 19a and the trap column 21, and to insert the tip of the needle 19b into the needle port of the inlet end 22 of the trap column 21, so that the passage 18b is connected to the trap column 21. In addition, the controller 52 drives the fraction collector head 35 so as to pull off the discharge nozzle 37 from the disposal port 39 and insert the discharge nozzle 37 into the collection container 38. In this state, the supply pump 16 is operated to supply a liquid at a predetermined constant flow rate. Then, the supply pump 16 draws the dichloromethane held in the eluting solvent container 13 and supplies it through the inlet end 22 into the trap column 21. Since dichloromethane has a strong elution power, while the dichloromethane passes through the trap column 21, the target component that is captured by the grains of filler will dissolve in the dichloromethane. Then, the dichloromethane containing the target component is discharged through the outlet end 23 and passes through the discharge passage 32 and the discharge nozzle 37 to be collected in the collection container 38.

Dichloromethane has a strong elution power. Therefore, the eluate containing the target component at a high concentration flows through the discharge passage 32. Hence, the target component easily deposits in the passage, which may clog the pipes and valves, impeding the smooth flow of the eluate. However, in the system of the present embodiment, in this operation, during a predetermined time period from the point in time when the eluting solvent starts to be discharged from the outlet end of the trap column 21, the controller 52 controls the selector valve 17 so as to intermittently change the passage from the needle 18b side (port g) to the dilution passage 15 side (port f), so that dichloromethane drawn by the supply pump 16 is directly sent to the discharge passage 32 without passing through the trap column 21. As a result, the eluate containing the target component at high concentration is diluted, which makes it difficult for the deposition of the target component to occur in the discharge passage 32.

After the dichloromethane is supplied into the trap column 21 for a predetermined period of time or to a predetermined amount, the controller 52 halts the liquid supply operation of the supply pump 16 and disconnects the needle 19b and the trap column 21.

At this point in time, the components captured in the trap column 21 and other substances remain at a circumferential portion of the tips of the needles 19a and 19b. The controller 52 drives the base 40 by means of the triaxial drive mechanism 51 so as to simultaneously insert the needles 19a and 19b into the washing holes 61a and 61b. As a result, the openings 62a and 62b of the washing holes 61a and 61b are closed by the cap sections 64a and 64b provided on the outer circumferential surface of the needles 19a and 19b.

As previously described, the washing ports 60a and 60b are biased upwards by the elastic members 65a and 65b. Therefore, even in the case where there is a slight difference in the attachment heights of the cap sections 64a and 64b on the needles 19a and 19b, the height difference can be canceled by the elastic members 65a and 65b. Consequently, the outer circumferential surfaces of the cap sections 64a and 64b are tightly attached to the outer edges of the openings 62a and 62b.

While the washing holes 61a and 61b of the washing ports 60a and 60b are sealed as described above, the controller 52 first switches the selector valve 17 so as to connect the supply pump 16 (port e) to the passage 18a (port h), and energizes the supply pump 16. Then, the dichloromethane held in the solvent container 13 is drawn by the supply pump 16, passes through the passage 18a and the path 41a inside the needle 19a, and flows out from the tip of the needle 19a. For a better washing effect, the amount of the needle cleaning liquid (dichloromethane in this embodiment) is more than necessary to fill the washing hole 61a. In the needle washing mechanism according to the present embodiment, the needle cleaning liquid supplied in excess of the capacity of the washing hole 61a is discharged from the washing hole 61a via the disposal passage 63a, and passes through the disposal tube 72a to be collected in the disposal container 73.

After the residual components attached to the circumferential portion of the tip of the needle 19a are removed, the controller 52 switches the selector valve 17 so as to connect the supply pump 16 (port e) to the passage 18b (port g). As a result, the needle cleaning liquid (dichloromethane) passes through the passage 18b and the path 41b inside the needle 19b to be discharged from the tip of the needle 19b. In this manner, the needle cleaning liquid is supplied to the washing hole 61b of the washing port 60b, and the residual components attached to the circumferential portion of the tip of the needle 19b are removed.

As described above, in the preparative separation-purification system 1 according to the present embodiment, the dichloromethane held in the solvent container 13 is used not only as the eluting solvent but also as the needle cleaning liquid. That is, in the present embodiment, the eluting solvent container 13 holding dichloromethane, the selector valve 14, the supply pump 16, the passages 18a and 18b, and the selector valve 17 correspond to the needle cleaning liquid supply means of the present invention.

In the case where the completion of the washing of the needles 19a and 19b is followed by another preparative separation-purification operation using a different trap column on the column rack 20, the controller 52 drives the base 40 so that the needle 19a is connected to the inlet end of the next trap column. The controller 52 also drives the fraction collector head 35 so that the needle 31 is connected to the outlet end 23 of the next trap column, and the discharge nozzle 37 is inserted into the next collection container. Then, the solution container 11 is replaced by a container holding another solution (which contains the target component for the following preparative separation-purification), and the preparative separation-purification operation as previously described is performed. By the time of the initiation of this new operation, the residual components attached to the circumferential portion of the tip of the needles 19a and 19b have been completely removed. Connecting the needles 19a and 19b to the inlet end of the next trap column will not cause a contamination.

As described above, with the needle washing mechanism according to the present embodiment, when washing the needles 19a and 19b, the washing holes 61a and 61b are sealed by the cap sections 64a and 64b, and the used needle cleaning liquid passes through the washing holes 61a and 61b and the disposal passages 63a and 63b to be collected in the disposal container 73. Therefore, the needle cleaning liquid will not volatize or diffuse into the air, which allows a volatile organic solvent having an environmental toxicity such as dichloromethane, which was described above, to be used as the needle cleaning liquid. This configuration allows the selection of an appropriate needle cleaning liquid without having to take into consideration the volatility according to the kind of the residual components which are attached (or expected to be attached) to the circumferential portion of the tips of the needles 19a and 19b, ensuring a washing of the needles 19a and 19b.

Thus far, the best mode for carrying out the present invention has been described using an embodiment. However, the present invention is not limited by the embodiment, and may be appropriately changed within the spirit of the present invention.

Figure 3:
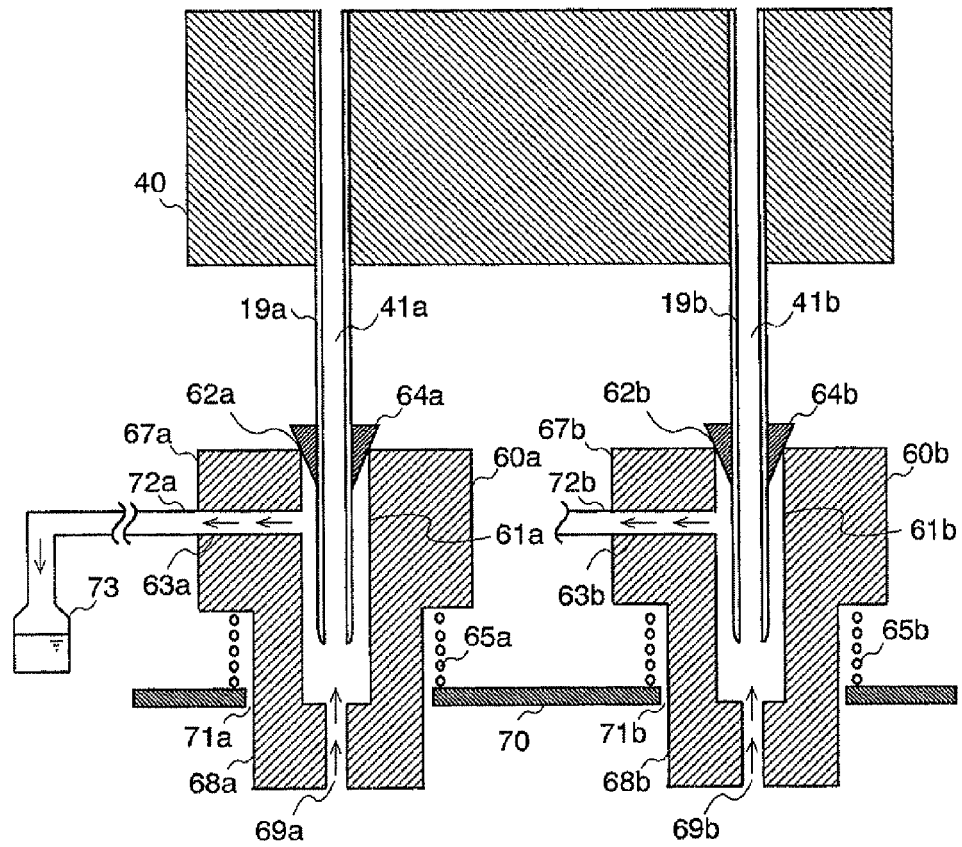
FIG. 3 is a vertical sectional view of a needle washing mechanism according to a modification example of the present invention.
Figure 4:
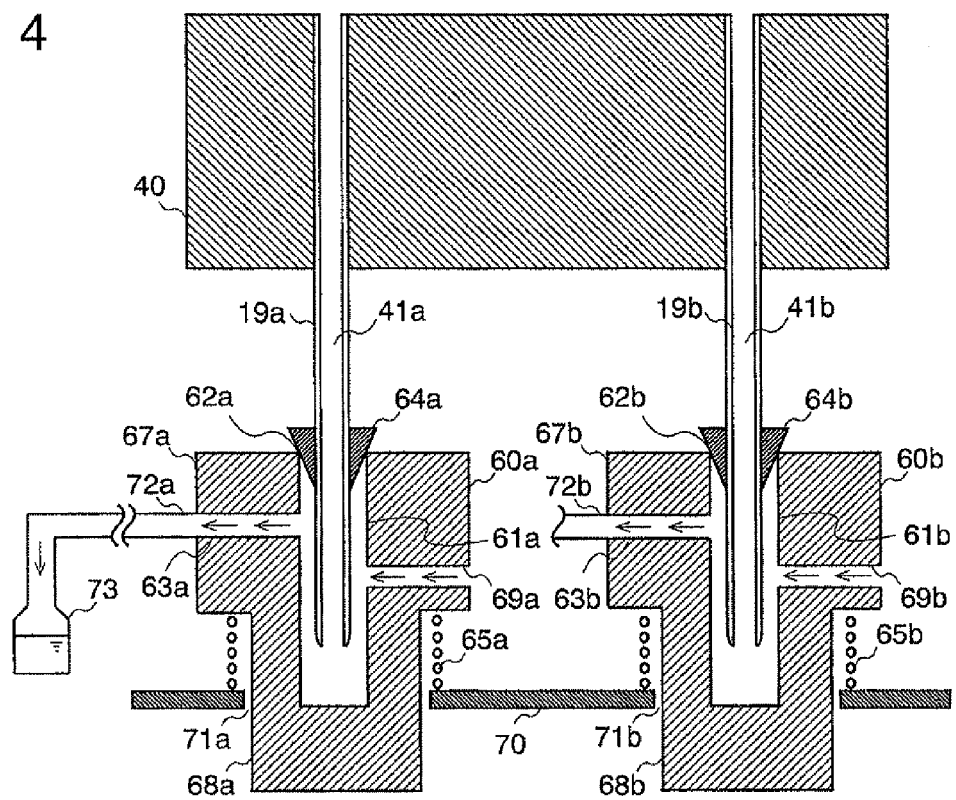
FIG. 4 is a vertical sectional view of a needle washing mechanism according to another modification example of the present invention.
Figure 5:
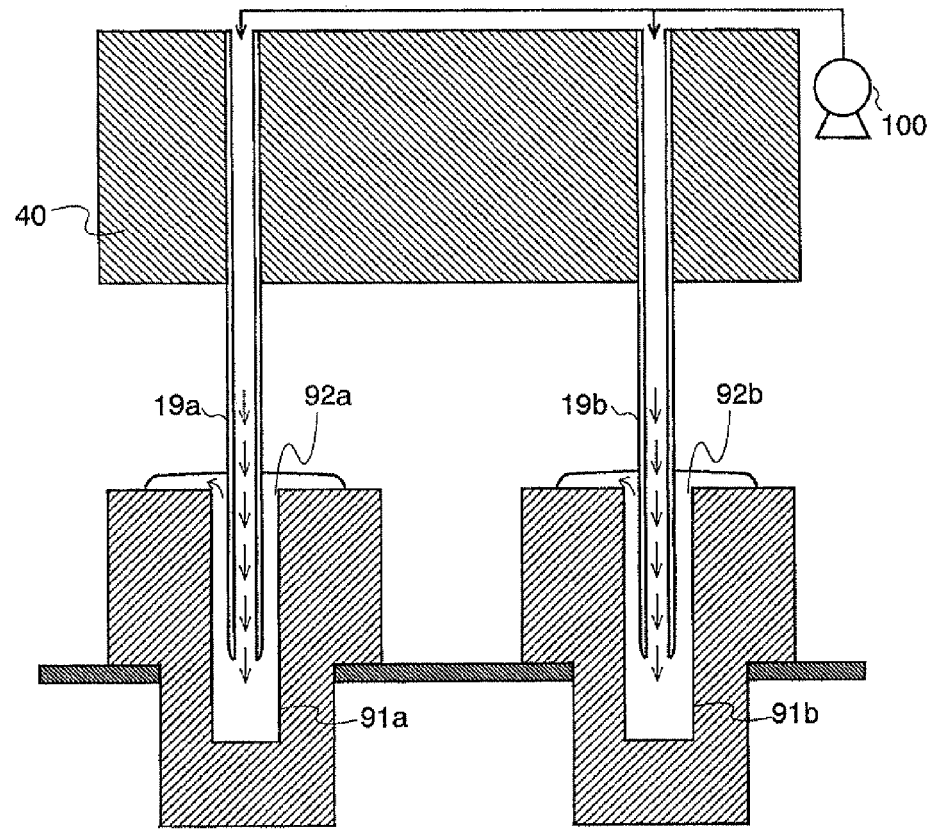
FIG. 5 is a vertical sectional view of a conventional needle washing mechanism.

FIG. 3 shows a modification example of the needle washing mechanism according to the present invention. The needle washing mechanism according to the present modification example has needle cleaning liquid supply passages 69a and 69b which are open on the inner circumferential surface of the washing holes 61a and 61b. The needle cleaning liquid is supplied into the washing holes 61a and 61b not via the paths 41a and 41b of the needles 19a and 19b, but via the needle cleaning liquid supply passages 69a and 69b. Alternatively, as shown in FIG. 4, the needle cleaning liquid supply passages 69a and 69b may be open on the inner circumferential surface of the washing holes 61a and 61b.

In the above-described embodiment, dichloromethane, which acts as the eluting solvent, is also used as the needle cleaning liquid. However, a liquid which is different from the eluting solvent may be used as the needle cleaning liquid. In this case, in addition to the aforementioned eluting solvent container 13 and the supply pump 16, a container for the needle cleaning liquid and a supply pump are provided so that the needle cleaning liquid drawn from the container by the supply pump is supplied to the washing holes 61a and 61b.

In the above-described embodiment, the needle cleaning liquid is supplied to the plurality of washing ports one by one. However, the method of supplying the needle cleaning liquid is not limited thereto: it may be supplied simultaneously to the plurality of washing ports.

The needle washing mechanism of the present embodiment can be applied not only in the preparative separation-purification system described above, but also in a liquid chromatograph apparatus, an auto sampler, or other apparatuses.

EXPLANATION OF NUMERALS

1 . . . Preparative Separation-Purification System
11 . . . Solution Container
12 . . . Column Wash Solution Container
13 . . . Eluting Solvent Container
14, 17 . . . Selector Valve
15 . . . Dilution Passage
16 . . . Supply Pump
19a, 19b, 31 . . . Needle
20 . . . Column Rack
21 . . . Trap Column
22 . . . Inlet End
23 . . . Outlet End
32 . . . Discharge Passage
33 . . . T-Joint
37 . . . Discharge Nozzle
38 . . . Collection Container
39 . . . Disposal Port
40 . . . Base
41a, 41b . . . Path
51 . . . Triaxial Drive Mechanism
52 . . . Controller
53 . . . Operation Unit
60a, 60b . . . Washing Port
61a, 61b, 91a, 91b . . . Washing Hole
62a, 62b, 92a, 92b . . . Opening
63a, 63b . . . Disposal Passage
64a, 64b . . . Cap Section
65a, 65b . . . Elastic Member
67a, 67b Upper Portion
68a, 68b Lower Portion
69a, 69b . . . Needle Cleaning Liquid Supply Passage
70 . . . Bottom Plate
71a, 71b . . . Through-Hole
72a, 72b . . . Disposal Tube
73 . . . Disposal Container

The invention claimed is:

1. A needle washing mechanism having: a plurality of needles which stand on a base side by side and each of which has a path inside thereof through which a liquid passes; a plurality of washing ports each of which includes a washing hole having an opening into which any one of the needles is inserted; and a needle cleaning liquid supply means for supplying a needle cleaning liquid to each of the washing holes, the needle washing mechanism comprising:
   a) a cap section, which is provided on an outer circumferential surface of each of the plurality of needles, for closing the opening of each of the washing holes when the needle is inserted into the washing hole;
   b) a biasing means for biasing each of the plurality of washing ports toward the opening; and
   c) a disposal passage, which is provided in the washing port, for discharging the needle cleaning liquid from each of the plurality of the washing holes.

2. The needle washing mechanism according to claim 1, wherein the needle cleaning liquid supply means supplies the needle cleaning liquid to each of the washing holes through the path provided in the needles.

3. The needle washing mechanism according to claim 1, wherein the needle cleaning liquid supply means supplies the needle cleaning liquid to each of the washing holes through a needle cleaning liquid supply passage which is open on an inner circumferential surface or on an inner bottom surface of the washing holes.

4. The needle washing mechanism according to claim 1, wherein the cap section has a tapered shape which becomes thinner toward a tip of the needle.

5. The needle washing mechanism according to claim 2, wherein the cap section has a tapered shape which becomes thinner toward a tip of the needle.

6. The needle washing mechanism according to claim 3, wherein the cap section has a tapered shape which becomes thinner toward a tip of the needle.

* * * * *